(12) United States Patent
Miller et al.

(10) Patent No.: US 6,638,943 B2
(45) Date of Patent: Oct. 28, 2003

(54) YOHIMBINE DIMERS EXHIBITING BINDING SELECTIVITIES FOR $\alpha_2$ ADRENERGIC RECEPTORS

(75) Inventors: Duane D. Miller, Germantown, TN (US); Weiping Zheng, Baltimore, MD (US); Bob M. Moore, II, Nesbit, MS (US); Suni Mustafa, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/106,521

(22) Filed: Mar. 25, 2002

(65) Prior Publication Data

US 2003/0036547 A1 Feb. 20, 2003

Related U.S. Application Data

(60) Provisional application No. 60/278,181, filed on Mar. 23, 2001.

(51) Int. Cl.[7] .................. A61K 31/475; C07D 459/00
(52) U.S. Cl. ..................... 514/280; 546/53; 546/50
(58) Field of Search ........................... 514/280; 546/53, 546/50

(56) References Cited

U.S. PATENT DOCUMENTS 3,940,387 A 2/1976 Saint-Ruf et al.

OTHER PUBLICATIONS

Zheng, W. et al. : Yohimbine dimers exhibiting binding selectives for human alpha 2a versus alpha 2b adrenergic receptors. Bioorg. & Medicin. Chem. Lett. vol. 10, pp. 627–630, 2000.*

Portoghese et al., "Stereostructure–Activity Relationship of Opioid Agonist and Antagonist Bivalent Ligands. Evidence for Bridging Between Vicinal Opioid Receptors," *J. Med. Chem.* 28:1140–41 (1985).

Erez et al., "Narcotic Antagonist Potency of Bivalent Ligands Which Contain β–Naltrexamine. Evidence for Bridging Between Proximal Recognition Sites," *J. Med. Chem.* 25:847–849 (1982).

Philip S. Portoghese, "The Role of Concepts in Structure–Activity Relationship Studies of Opioid Ligands," *Journal of Medicinal Chemistry* 35(11):1927–1937 (1992).

Philip S. Portoghese, Bivalent Ligands and the Message–Address Concept in the Design of Selective Opioid Receptor Antagonists, *TIPS Review* 10:230–235 (1989).

Shimohigashi et al., "Dimeric Tetrapeptide Enkephalins Display Extraordinary Selectivity for the δ Opiate Receptor," *Nature* 297:333–335 (1982).

LeBoulluec et al., "Bivalent Indoles Exhibiting Serotonergic Binding Affinity," *Bioorganic & Medicinal Chemistry Letters*, 5:123–126 (1995).

Cwirla et al., "Peptide Agonist of the Thrombopoietin Receptor as Potent as the Natural Cytokine," *Science* 276:1696–1699 (1997).

Uhlén et al., "Membrane Organization and Mobility of $\alpha_2$ Adrenergic Receptors in MDCK Cells," *Pharmacology Communications* 6(1–3):155–167 (1995).

Maggio et al., "Coexpression Studies with Mutant Muscarinic/Adrenergic Receptors Provide Evidence for Intermolecular "Cross–Talk" Between G–Protein–Linked Receptors," *Proc. Natl. Acad. Sci. USA* 90:3103–3107 (1993).

Maggio et al., "Functional Role of the Third Cytoplasmic Loop in Muscarinic Receptor Dimerization," *The Journal of Biological Chemistry* 27(49):31055–31060 (1996).

Zheng, et al., "Yohimbine Dimers Exhibiting Binding Selectives for Human $\alpha_{2a}$—versus $\alpha_{2b}$—Adrenergic Receptors," *Biorg. Med. Chem. Lett.* 10:627–630 (2000).

* cited by examiner

*Primary Examiner*—Charanjit. S. Aulakh
(74) *Attorney, Agent, or Firm*—Nixon Peabody LLP (57) ABSTRACT

The present invention relates to yohimbine dimer compounds, pharmaceutical compositions containing such dimer compounds, methods of making such dimer compounds, and uses thereof. The yohimbine dimer compounds include compounds of formula (I):

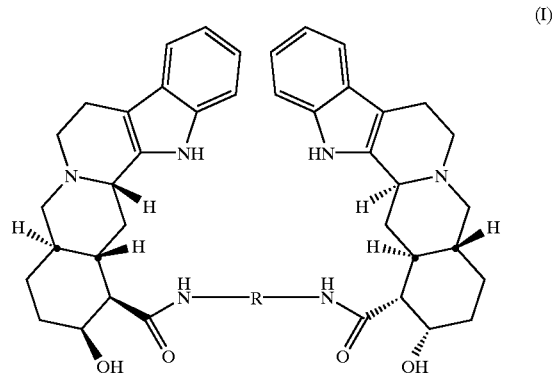

(I)

where R is any linker molecule which affords a yohimbine dimer that has activity as an $\alpha_2$-AR antagonist and has selectivity for an $\alpha_2$-AR subtype over another $\alpha_2$-AR subtype.

26 Claims, 1 Drawing Sheet pK$_i$ Values versus the Dimer length for Yohimbine Analogs

YOHIMBINE DIMERS EXHIBITING BINDING SELECTIVITIES FOR $\alpha_2$ ADRENERGIC RECEPTORS This application claims the benefit of U.S. Provisional Application Ser. No. 60/278,181, filed Mar. 23, 2001, which is hereby incorporated by reference in its entirety.

This work was supported by the National Institutes of Health, Grant No. NIH R01 GM 29358. The U.S. Government may have certain rights in this invention.

FIELD OF THE INVENTION

The present invention relates to yohimbine dimer compounds, pharmaceutical compositions containing such compounds, methods of making such compounds, as well as various uses thereof.

BACKGROUND OF THE INVENTION

The initial classification of adrenergic receptors (AR's) into $\alpha$- and $\beta$-families was first described by Ahlquist in 1948 (Ahlquist RP, "A Study of the Adrenergic Receptors," *Am. J. Physiol.* 153:586–600 (1948)). Functionally, the $\alpha$-ARs were shown to be associated with most of the excitatory functions (vasoconstriction, stimulation of the uterus and pupil dilation) and inhibition of the intestine. On the other hand, $\beta$-ARs were implicated in vasodilation, bronchodilation and myocardial stimulation (Lands et al., "Differentiation of Receptor Systems Activated by Sympathomimetic amines," *Nature* 214:597–598 (1967)). Since this early work, $\alpha$-ARs have been subdivided into $\alpha_1$- and $\alpha_2$-AR. Cloning and expression of $\alpha$-AR have confirmed the presence of multiple subtypes of both $\alpha_1$-($\alpha_{1a}$, $\alpha_{1b}$, $\alpha_{1d}$) and $\alpha_2$-($\alpha_{2a}$, $\alpha_{2b}$, $\alpha_{2c}$) AR (Michel et al., "Classification of $\alpha_1$-Adrenoceptor Subtypes," *Naunyn-Schmiedeberg's Arch. Pharmacol,* 352:1–10 (1995); Macdonald et al., "Gene Targeting—Homing in on $\alpha_2$-Adrenoceptor-Subtype Function," *TIPS,* 18:211–219 (1997)).

In humans, the three $\alpha_2$-AR subtypes are encoded by distinct genes localized in different chromosomes. The $\alpha_{2a}$-AR gene is located in chromosome 10, while the $\alpha_{2b}$-AR gene is found on chromosome 2 and the $\alpha_{2c}$-AR gene on chromosome 4 (Bylund et al., "International Union of Pharmacology Nomenclature of Adrenoceptors," *Pharmacol. Rev.,* 46:121–142 (1994)).

Current therapeutic uses of $\alpha_2$-ARs drugs involve the ability of those drugs to mediate many of the physiological actions of the endogenous catecholamines and there are many drugs that act on these receptors to control hypertension, analgesia, anesthesia, and ocular and nasal congestion.

$\alpha_2$-ARs are found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," *Eur. J. Pharmacol.,* 34:151–156 (1975); Bousquet et al., "Imidazoline Receptors: From Basic Concepts to Recent Developments," 26:S1–S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1–S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1–S6 (1995); Reis et al., "The Imidazoline Receptor: Pharmacology, Functions, Ligands, and Relevance to Biology and Medicine," *Ann. N.Y. Acad. Sci.,* 763:1–703 (1995); Diamant et al., "Imidazoline Binding Sites in Human Placenta: Evidence for Heterogeneity and a Search for Physiological Function," *Br. J. Pharmacol.,* 106:101–108 (1992); Ragunathan et al., "Imidazoline Receptors and Their Endogenous Ligands," *Annu. Rev. Pharmacol. Toxicol.,* 36:511–544 (1996); Miralles et al., "Discrimination and Pharmacological Characterization of $I_2$-Imidazoline Sites with [$^3$H] idazoxan and Alpha-2-Adrenoceptors [$^3$H]RX821002 (2 Methoxy Idazoxan) in Human and Rat Brains," *J. Pharmacol. Exp. Ther.,* 264:1187–1197 (1993)). The pharmacological profiles of drugs acting on imidazoline receptors have resulted in their classification into two main types: $I_1$- and $I_2$-imidazoline binding sites (Diamant et al., "Imidazoline Binding Sites in Human Placenta: Evidence for Heterogeneity and a Search for Physiological Function," *Br. J. Pharmacol.,* 106:101–108 (1992); Miralles et al., "Discrimination and Pharmacological Characterization of $I_2$-Imidazoline Sites with [$^3$H]idazoxan and Alpha-2-Adrenoceptors [$^3$H]RX821002 (2 Methoxy Idazoxan) in Human and Rat Brains," *J. Pharmacol. Exp. Ther.,* 264:1187–1197 (1993); Olmos et al., "Pharmacological and Molecular Discrimination of Brain $I_2$-Imidazoline Receptor Subtypes," *Naunyn-Schmiedberg's Arch. Pharmacol.,* 354:709–716 (1996)).

Yohimbine is a known potent and selective $\alpha_2$-AR antagonist, and has been used extensively as a pharmacological probe for studying the $\alpha_2$-AR (Starke K., *Rev. Physiol. Biochem. Pharmacol,* 88, 199 (1981)). Yohimbine, an indole alkaloid isolated from Pausinystlia yohimbe bark and Rauwolfia roots, is an $\alpha_2$-antagonist selective for $\alpha_2$ over $\alpha_1$ adrenoreceptors, but is also a serotonic antagonist. It has actions both in the central nervous system and in the periphery inducing hypertension and increases heart rate. Yohimbine has been used to treat male impotence and posturalo hypotension. It has also been used in research to induce anxiety (Foye et al. *Principles of Medicinal Chemistry,* Fourth Edition, Williams & Wilkins (1995), page 359). However, yohimbine does not show selectivity among three $\alpha_2$-AR subtypes (Hieble et al., *J. Med. Chem.,* 38, 3415 (1995); Hieble et al., *Prog. Drug Res.,* 47, 81 (1996)).

Although there have been a number of $\alpha_2$-AR antagonists identified (Ruffolo et al., *J. Med. Chem.,* 38, 3681 (1995); Clark et al., *Prog. Med. Chem.,* 23, 1 (1986)), only a small set of compounds have been reported that have a varied degree of selectivity among the three subtypes of $\alpha_2$-AR. However, these latter compounds suffer from either low subtype selectivity or binding to receptor sites outside the $\alpha_2$-AR subfamily (Ruffolo et al., *J. Med. Chem.,* 38, 3681 (1995; Yound et al, *Eur. J. Pharmacol.,* 168, 381 (1989); Devedjian et al, *Eur. J. Pharmacol.,* 252, 43 (1994); Meana et al., *Eur. J. Pharmacol.,* 312, 385 (1996); Beeley et al., *Bioorg. Med. Chem.,* 3, 1693 (1995); Michel et al., *Br. J. Pharmacol.,* 99, 560 (1990); Uhlen et al., *Pharmacol. Exp. Ther.,* 271, 1558 (1994); Blaxall et al., *Pharmacol. Exp. Ther.,* 259, 353 (1991); Bylund et al., *Mol. Pharmacol.,* 42, 1 (1992); Okumura et al, *Gen. Pharmacol.,* 19, 463 (1988)). Thus, a need exists to identify compounds which bind $\alpha_2$-AR subtypes with sufficient affinity and selectivity.

The present invention is directed to overcoming these and other problems encountered in the art.

SUMMARY OF THE INVENTION

The present invention relates to a compound according to formula (I):

(I)

wherein R is a linker molecule, preferably having a length of about 2.5 Å to about 45 Å.

The present invention also relates to a compound according to formula (I), wherein R (i.e., as a linker molecule) is a straight or branched chain alkyl, alkenyl, alkynyl comprising at least 2 carbon atoms in a main chain thereof; wherein R (i.e., as a linker molecule) is a straight or branched chain alkyl, alkenyl, alkynyl comprising at least 2 carbon atoms in a main chain thereof and an X group within the main chain and/or a Y group as a substituent linked to a carbon atom in the main chain with X being —O—, carbonyl, —NR$^1$— with R$^1$ being H or an alkyl, C(O)NHR$^1$— with R$^1$ being an alkyl, —S—, sulfoxide, sulfonyl, or a cyclic or multicyclic ring with or without heteroatoms as ring members and including, optionally, one or more substitutions on the ring structure(s), and with Y being —OH, —NO$_2$, —CN, —C(O)H, —SH, or a primary, secondary, or tertiary amine, a carboxylic acid, an ester, a keto group, —SO$_2$NH$_2$, or —SO$_2$NHR$^2$ with R$^2$ being an alkyl; or wherein R (i.e., as a linker molecule) is a cyclic or multicyclic ring with or without hetero atoms as ring members and including, optionally, one or more substitutions on the ring structure(s).

The present invention also relates to a pharmaceutical composition, which includes a yohimbine dimer of the present invention and a pharmaceutically acceptable carrier.

The present invention further relates to a method of making a yohimbine dimer of the present invention, which includes reacting yohimbic acid with a di-amine according to the formula H$_2$N—R—NH$_2$ under conditions effective to yield a yohimbine dimer of the present invention.

Yet another aspect of the present invention relates to a method of treating or preventing an α$_2$ adrenergic receptor mediated condition or disorder which includes: administering to a patient an effective amount of a yohimbine dimer of the present invention under conditions effective to treat or prevent the α$_2$ adrenergic receptor mediated condition or disorder.

A further aspect of the present invention relates to a method of modulating the activity of an α$_{2a}$ adrenergic receptor which includes: contacting an α$_{2a}$ adrenergic receptor with a yohimbine dimer of the present invention under conditions effective to modulate the activity of the α$_{2a}$ adrenergic receptor.

A still further aspect of the present invention relates to a method of modulating the activity of an α$_{2c}$ adrenergic receptor which includes: contacting an α$_{2c}$ adrenergic receptor with a yohimbine dimer of the present invention under conditions effective to modulate the activity of the α$_{2c}$ adrenergic receptor.

The present invention provides additional advantages because it identifies a bivalent ligand approach to identify α$_2$-AR subtype-selective antagonists. As demonstrated herein, the bivalent yohimbine ligands exhibit a higher degree of potency, binding affinity, and selectivity than their monovalent counterparts.

DETAILED DESCRIPTION OF THE INVENTION

The present invention relates to a compound according to formula (I):

(I)

where R is any linker molecule which affords a yohimbine dimer that has activity as an α$_2$-AR antagonist and, specifically, has selectivity for one α$_2$-AR subtype over another α$_2$-AR subtype. Preferably, the yohimbine dimer compounds of the present invention either have selectivity for (i) the α$_{2a}$-AR over the α$_{2b}$-AR, or (ii) the α$_{2c}$-AR over the α$_{2b}$-AR. Depending on the length of the linker molecule, selectivity between the α$_{2c}$-AR and α$_{2a}$-AR can also be achieved.

According to one aspect of this invention, R is a linker molecule, wherein R is (i) a straight or branched chain alkyl, alkenyl, alkynyl including at least 2 carbon atoms in a main chain thereof; (ii) a straight or branched chain alkyl, alkenyl, alkynyl comprising at least 2 carbon atoms in a main chain thereof and an X group within the main chain and/or a Y group as a substituent linked to a carbon atom in the main chain, with X being —O—, carbonyl, —NR$^1$— with R$^1$ being H or an alkyl, —C(O)NHR$^1$— with R$^1$ being an alkyl, —S—, sulfoxide, sulfonyl, or a cyclic or multicyclic ring with or without hetero atoms as ring members and including, optionally, one or more substitutions on the ring structure(s) and with Y being —OH, —NO$_2$, —CN, —C(O)H, —SH, or a primary, secondary, or tertiary amine, a carboxylic acid, an ester, a keto group, —SO$_2$NH$_2$, or —SO$_2$NHR$^2$ with R$^2$ being an alkyl; or (iii) a cyclic or multicyclic ring with or without hetero atoms as ring members and including, optionally, one or more substitutions on the ring structure(s).

According to a second aspect, R is a linker molecule having a length of about 2.5 Å to about 45 Å, more preferably within a first range of about 2.5 Å to about 5 Å or a second range of about 23 Å to about 29 Å.

In accordance with the present invention, suitable chemical starting materials, such as different reactants, reagents, such as compounds with different chemical functional substituent groups, that combine to form the bivalent yohimbine dimer compounds of formula (I) are defined below. Such reactant compounds include, without limitation, yohimbic acid and its corresponding derivatives.

Suitable for use in the present invention are a yohimbine compound, which is conventionally known in the literature as a indole alkaloid and any corresponding yohimbine derivatives (i.e., substituted with different chemical group substituents) as prepared or synthesized by known organic synthetic methods. Preferably the yohimbine compound (or its derivative) is in the form of a yohimbic acid.

Yohimbic acid, as noted hereinafter, is reacted with a diamine $H_2N$—R—$NH_2$, where R is a linker molecule of the type described above.

In the present invention, R and/or $R^1$ are defined as straight or branched chain alkyls, which include at least 2 carbons in a main chain thereof. Straight chain alkyl groups which are represent by the formula —$(CH_2)_n$—, which is a methylene unit functional group fragment, where n is an integer of greater than or equal to 2 units (i.e. $n \geq 2$). Branched chain alkyls may have the formula as defined above for a straight chain alkyl, except that one or more $CH_2$ groups may be replaced by —$(CHW)_n$— groups wherein W represents an alkyl side chain.

A preferred embodiment for chain representations is where the term n is defined as being an integer of at least 2, preferably n is an integer from at least 2 to 36 units, more preferably from 3 to 36 units. In alternate preferred embodiments of the present invention, compounds of the present invention have straight or branched alkyl groups, wherein n is an integer greater than or equal to 18, more preferably greater than or equal to an integer from 24 to 36.

In the present invention, R may be defined as a straight or branched chain alkenyl group, which includes at least 5 carbons in a main chain thereof. In accordance with the present invention, straight chain alkenyls may be represented by the formula —$(CH_2)_{xa}CH=CH(CH_2)_{xb}$— where xa and xb each are independently defined as integers that may be greater than or equal to the integer zero (i.e., xa and xb$\geq$0), xa and xb being the same or different. Branched chain alkenyls have the formula as defined above for straight chain alkenyl, except that one or more $CH_2$ groups, may be replaced by CHW groups or a CH group is replaced by a CW group, where W is an alkyl side chain.

In the present invention, R may also be defined as a straight or branched chain alkynyl group, which includes at least 5 carbon atoms in a main chain thereof. Suitable for use in the present invention, straight chain alkynyl groups are represented by the formula —$(CH_2)_{xc}C\equiv C(CH_2)_{xd}$— where xc and xd each are independently defined as integers that may be greater than or equal to the integer zero (i.e., xc and xd$\geq$0), with xc and xd being the same or different. In addition, branched chain alkynyls have the formula as defined above for straight chain alkynyl groups, except that one or more $CH_2$ groups are replaced by CHW groups, where W is an alkyl side chain, i.e., as represented by the formula —$(CHW)_{xc}C\equiv C(CHW)_{xd}$—.

In accordance with the present invention, R may be a straight or branched chain alkyl, alkenyl, alkynyl with at least 2 carbon atoms in a main chain thereof and an X group within the main chain and/or a Y group as a substituent linked to a carbon atom in the main chain. X can be —O—, carbonyl, —$NR^1$— with $R^1$ being an alkyl, —$C(O)NHR^1$— with $R^1$ being an alkyl, —S—, sulfoxide, sulfonyl, or a cyclic or muticyclic ring with or without hetero atoms as ring members and including, optionally, one or more substitutions on the ring structure(s). Y can be —OH, —$NO_2$, —CN, —C(O)H, —SH, a primary, secondary, or tertiary amine, a carboxylic acid, an ester, a keto group, —$SO_2NH_2$, or —$SO_2NHR^2$ with $R^2$ being an alkyl.

In addition, R can be a cyclic or multicyclic ring with or without hetero atoms as ring members and including, optionally, one or more substitutions on the ring structures.

Cyclic or multicyclic rings (whether defined as R or as X above) can be aromatic or non-aromatic, either with or without N, S, or O hetero ring members, including without limitation, cycloalkanes, cycloalkenes, phenyls, indenes, pyrroles, imidazoles, oxazoles, pyrrazoles, pyridines, pyrimidines, pyrrolidines, piperidines, thiophenes, furans, napthals, bi-phenyls, indoles, tetrahydrofurans, decalins, and tetrahydrothiophenes.

The cyclic or multicyclic rings suitable for use in the present invention can include mono-, di-, tri or multiple additional substitutions of each different ring type, where standard organic chemistry principles, such as valency permit. In the case of aromatic, heteroaromatic rings and the like, additional chemical functional group substituents may include mono-, di-, or tri-substitutions of each different ring type, which may be located at the ortho, meta, or para positions on such cyclic ring systems relative to where the ring is positioned within a R group substituent. An exemplary aromatic cyclic group bearing alkyl-substitutions at para positions is

In accordance with the present invention, additional functional group substitutions on such ring systems may include, without limitation, alkyl, alkoxy, acylalkyl, halogen, mercapto, nitro, bydroxy, aldehyde, carboxylic acids, primary, secondary, or tertiary amines, and ketones.

According to one embodiment, a bivalent yohimbine dimer compound of the present invention includes an R group which may be a straight chain alkyl comprising at least 4 carbon atoms in a main chain thereof and an X group within the main chain, wherein X is a —O—. Such an R group may be represented by —$(CH_2—CH_2—O—CH_2—CH_2)_n$— where n is an integer from 1 to 6. For example, an alkyl group bearing an X group in the main chain is —$(CH_2)_4$—O—$(CH_2)_4$—. Another example is represented by —$(CH_2—CH_2—O—CH_2—CH_2—O—CH_2—CH_2)_n$— wherein n is an integer from 1 to 4. Moreover, an exemplary R group that is an alkyl group bearing a Y group as a substituent is —$(CH_2)_4$—CH(OH)—$(CH_2)_4$—.

In another embodiment, a bivalent yohimbine dimer compound of the present invention includes an R group which is a straight chain alkyl comprising at least 5 carbon atoms in a main chain thereof and an X group within the main chain, wherein X is —$C(O)NHR^1$— with $R^1$ being an alkyl. Such an R group can be represented by —$(CH_2—NHC(O))_n$—$CH_2—CH_2—CH_2—CH_2—(C(O)NH—CH_2)_n$— wherein each n is independently an integer from 1 to 3.

In another embodiment of the present invention, a bivalent yohimbine dimer compound includes an R group that is a cis isomer or a trans isomer of —$(CH_2—NHC(O))_n$—

$CH_2$—CH=CH—$CH_2$—(C(O)NH—$CH_2)_n$— wherein each n is independently an integer from 1 to 3. An R group represented by the cis isomer is wherein each n is independently an integer from 1 to 3. An R group represented by the trans isomer is wherein each n is independently an integer from 1 to 3.

Another aspect of the present invention relates to a method of making a yohimbine dimer, which includes reacting yohimbic acid and/or its corresponding derivatives with a di-amine and/or its corresponding derivatives according to the formula $H_2N$—R—$NH_2$ under conditions effective to yield a yohimbine dimer according to formula (I) as previously described. In particular, an initial reactant for forming the yohimbine dimer of the present invention, a compound which is a diamine having the formula $H_2N$—R—$NH_2$ is needed, where R is the same defined as above.

Suitable conditions effective to yield a yohimbine dimer according to Formula I of the present invention, include the use of conventional starting materials, reagents, solvents and/or reaction conditions, etc. as described below.

Many such diamines are commercially available or otherwise readily synthesizable according to conventional art known synthetic organic chemical techniques and/or procedures. For example, commercially available diamines include, without limitation, ethylene diamine, 1,2-propane diamine, 1,3-pentane diamine, 1,6-hexane diamine, p-phenylene diamine, napthalene 2,6-diamine, 2,4-toluene diamine, piperazine, 4,4'bis(dimethylamino)benzophenone, spermidine, putricine, cadaverine, or other natural polyamines.

According to one approach, standard peptide coupling procedures can be employed. For example, commercially available yohimbic acid can be reacted with aliphatic diamines with the intervening methylene groups ranging from about 2 to about 36 under standard peptide coupling (DCC,HOBT) conditions.

The method for the synthesis of compounds of the present invention can be carried out in an organic solvent. Conventional organic solvents can be used, which include, but are not limited to toluene, methyl-tert-butyl ether, pyridine, chloroform, methylene chloride, acetonitrile, N,N-dimethyl formamide ("DMF"), glymes, tetrahydrofuran ("THF"), isooctane, and mixtures of these solvents.

Alternatively, a variety of amide formation processes can be employed, using acid halides, carboxylic acid anhydrides, or carboxylic acids with heat and appropriate amines or diamines.

The reaction of the present invention can be carried out at a range of suitable temperatures, such as from 0° C. to 150° C., more preferably at 0° C. to 80° C. Optimal reaction temperatures can be selected based upon the particular choices of solvents and reactants.

The compounds prepared by the methods of the present invention can be pharmaceutically acceptable salts in the form of inorganic or organic acid or base addition salts of the above compounds. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, anthranilic, cinnamic, salicylic, 4-aminosalicylic, 2-phenoxybenzoic, 2-acetoxybenzoic, and mandelic acid. Sulfonic acids, such as, methanesulfonic, ethanesulfonic, and α-hydroxyethanesulfonic acid are also suitable acids. Non-toxic salts of the compounds of the above-identified formulae formed with inorganic and organic bases include, for example, those alkali metals, such as, sodium, potassium, and lithium, alkaline earth metals, for example, calcium and magnesium, light metals of group IIIA, for example, aluminum, organic amines, such as, primary, secondary, or tertiary amines, for example, cyclohexylamine, ethylamine, pyridine, methylaminoethanol, and piperazine.

Another aspect of the present invention relates to a pharmaceutical composition, which includes a yohimbine dimer as described above and a pharmaceutically acceptable adjuvant, carrier, and/or excipient.

The compounds or compositions prepared according to the present invention can be used to treat warm blooded animals, such as mammals. Examples of such beings include, without limitation, humans, cats, dogs, horses, sheep, cows, pigs, lambs, rats, mice, and guinea pigs.

Conventional administration methods may be suitable for use in the present invention as described below.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art. The quantity of the compound or composition administered will vary depending on the patient and the mode of administration and can be any effective amount. Typical dosages include about 0.01 to about 100 mg/kg.body wt. The preferred dosages include about 0.01 to about 0.1 mg/kg.body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect. For example, the desired antihistamine, antiallergy, and bronchodilator effects can be obtained by consumption of a unit dosage form such as a tablet containing 1 to 50 mg of the compound of the present invention taken 1 to 4 times daily.

The compounds prepared by the methods of the present invention can be utilized as the biologically active components in pharmaceutical compositions.

Depending upon the treatment being effected, the compounds or compositions of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The yohimbine dimer compounds and/or pharmaceutical composition can also include, but are not limited to, suitable adjuvants, carriers, excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the adjuvants, carriers and/or excipients. For example, application to mucous membranes can be achieved with an aerosol spray containing small particles of a compound of this invention in a spray or dry powder form.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipients. Such adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The present invention also relates to modulating the activity of an $\alpha_2$-AR, preferably selectively modulating the activity of $\alpha_{2a}$-AR or $\alpha_{2c}$-AR versus $\alpha_{2b}$-AR. This aspect of the present invention can be achieved by contacting an $\alpha_{2a}$ or $\alpha_{2c}$ adrenergic receptor with a yohimbine dimer of the present invention under conditions effective to modulate the activity of the $\alpha_{2a}$ or $\alpha_{2c}$ adrenergic receptor, respectively.

In so modulating the activity of an $\alpha_{2a}$ or $\alpha_{2c}$ adrenergic receptor, it is possible to treat or prevent an a2 adrenergic receptor mediated condition or disorder of the type listed below. This can be achieved by administering to a patient an effective amount of a yohimbine dimer of the present invention under conditions effective to treat or prevent the $\alpha_2$ adrenergic receptor mediated condition or disorder. More specifically, to treat or prevent disorders or conditions which involve the hyperactivity of $\alpha_{2a}$-AR or activity of normally silent $\alpha_{2c}$-AR, these ARs can be selectively targeted relative to the $\alpha_{2b}$-AR. As a result, numerous side-effect associated with $\alpha_{2b}$-AR antagonism can be avoided. Concepts pertaining to such methods are described below.

Suitable conditions for the modulation of the $\alpha_2$ adrenergic receptor relate to the fact that $\alpha_2$ receptors are located both pre-synaptically at nerve terminals and post-synaptically as in vascular smooth muscles, platelets, pancreatic β-cells, and fat cells. Activation of the presynaptic receptors inhibit the release of norepinephrine by a negative feedback mechanism. Blockade of these receptors would therefore increase the release of norepinephrine.

Yohimbine is known to be an antagonist of $\alpha_2$AR. This invention is directed to yohimbine dimer compounds which are selective antagonists for human $\alpha_2$ receptors, showing excellent selectivity between either the $\alpha_{2a}$ or $\alpha_{2c}$ receptors and the $\alpha_{2b}$ receptors. Depending on the particular R group, selectivity between $\alpha_{2a}$ and $\alpha_{2c}$ receptors can also be achieved. Thus, the yohimbine dimers of the present invention are particularly well suited for selectively inhibiting $\alpha_{2a}$-AR activity, selectively inhibiting $\alpha_{2c}$-AR activity, or both. As a result, the present invention also relates to the use of these compounds for treating or preventing disorders which implicate hyperactivity of $\alpha_{2a}$ adrenergic receptors or the activity of normally silenced $\alpha_{2c}$ adrenergic receptors.

The $\alpha_{2a}$ adrenergic receptors have been implicated in hyper-/hypotension, pain, glaucoma, alcohol and drug withdrawal, rheumatoid arthritis, ischemia, migraine, cognitive deficiency, spasticity, diarrhea, and nasal congestion. Lakhlani et al., "Substitution of a Mutant $\alpha_{2a}$-adrenergic Receptor via 'Hit and Run' Gene targeting Reveals the Role of this Subtype in Sedative, Analgesic, and Anesthetic-sparing Responses In Vivo," *Proc Natl Acad Sci USA* 94(18):9950–5 (1997), which is hereby incorporated by reference in its entirety, provides definitive evidence that the a2a adrenergic receptor subtype is the primary mediator of clinically important central actions of $\alpha_2$ adrenergic receptor agonists. MacMillan et al., "Central Hypotensive Effects of $\alpha_{2a}$-adrenergic Receptor Subtype," *Science* 273(5276): 801–3 (1996), which is hereby incorporated by reference in its entirety, demonstrates that the $\alpha_{2a}$ adrenergic receptor subtype plays a principal role in the hypotensive response to $\alpha_2$ adrenergic receptor agonists. Likewise, Makaritsis et al., "Sympathoinhibitory Function of the $\alpha_{2a}$-adrenergic Receptor Subtype," *Hypertension* 34(3):403–407 (1999), which is hereby incorporated by reference in its entirety, demonstrates that the $\alpha_{2a}$ adrenergic receptor subtype exerts a sympathoinhibitory effect, and its loss leads to a hypertensive, hyperadrenergic state. Ongoing work by Limbird has demonstrated that the $\alpha_{2a}$ subtype plays a role in suppression of epileptogenesis, pain perception, sedation and anesthesia, control of blood pressure by the central nervous system, and depression/sensitivity to antidepressant agents.

In particular, two related disorders which can be treated or prevented by the $\alpha_{2a}$ adrenergic receptor antagonists of the present invention are hypotension (low blood pressure) and hypertension (high blood pressure). By targeting peripheral $\alpha_{2a}$ adrenergic receptors, the yohimbine dimers of the present invention can be used to treat hypertension. In contrast, by targeting $\alpha_{2a}$ adrenergic receptors of the central nervous system, the yohimbine dimers of the present invention can be used to treat hypotension.

Moreover, consistant with the use of yohimbine to treat erectile dysfunction in males, the compounds of the present invention can also be used to effect such treatment.

The $\alpha_{2c}$ adrenergic receptors have been implicated in Raynaud's disease. The remarkable role of $\alpha_{2c}$-ARs in vascular dysfunction has very recently been discovered. Analysis of cutaneous arteries at 37° C. confirms that $\alpha_{2c}$-ARs do not contribute to vasoconstriction. However, Flavahan and coworkers (Chotani et al., "Silent Alpha2c-Adrenergic Receptors Enable Cold-Induced Vasoconstriction in Cutaneous Arteries," *Heart and Circulatory Physiology*, 278:H1075–H1083 (2000); Flavahan et al., "Increased Alpha2-Adrenergic Constriction of Isolated Arterioles in Diffuse Scleroderma," *Arthritis and Rheumatism*, 43:1886–1890 (2000), each of these references is hereby incorporated by reference in its entirety) have shown that during cold-induced vasoconstriction (28° C.), the $\alpha_{2c}$-ARs are "no longer silent" and are proposed to be responsible for the vasospastic episodes in Raynaud's disease.

Recent studies in the mouse tail artery confirm the previous observations that the $\alpha_{2c}$-ARs are activated at lower temperatures (Chotani et al., "Silent Alpha2c-Adrenergic Receptors Enable Cold-Induced Vasoconstriction in Cutaneous Arteries," *Heart and Circulatory Physiology*, 278:H1075–H1083 (2000), which is herein incorporated by reference in its entirety). At 37° C., the vasoconstriction is mediated by ARs ($\alpha_{2a}$- and $\alpha_{2b}$-) while $\alpha_{2c}$-ARs are not, or minimally, involved. However, in a remarkable way, the augmented vasoconstrictor response at 28° C. to catecholamines is mediated primarily by the $\alpha_{2c}$-AR. This work implies that $\alpha_{2c}$-ARs are "silent" at 37° C., but are activated during cold-induced exposures, e.g. at 28° C.

The Flavahan group reported that cold induced vasoconstriction is related to an increased distribution of $\alpha_{2c}$-ARs from the Golgi apparatus to the cellular membranes (Jeyaraj et al., "Cooling Evokes Redistribution of Alpha2C-Adrenoceptors from Golgi to Plasma Membrane in Transfected Human Embryonic Kidney 293 Cells," *Mol. Pharmacol.*, 60:1195–200 (2001), which is herein incorporated by reference in its entirety). The mechanism that silences or suppresses the actions of the $\alpha_{2c}$-ARs at 37° C. is unknown. The specific temperature effect on the $\alpha_{2c}$-ARs could reflect altered membrane targeting or processing of the $\alpha_{2c}$-ARs or variations in the signaling or amplification process.

The "Raynaud's Disease Phenomenon" results from the vasospasms in the digital arterioles in response to cold, causing a sharp demarcated cutaneous pallor and cyanosis of the digits (Ekenvall et al., "Alpha-Adrenoceptors and Cold Induced Vasoconstriction in Human Finger Skin," *Am. J. Physiol.*, 255:H1000–H1003 (1988), which is herein incorporated by reference in its entirety). Studies with human patients show that vascular dysfunction is an important early defect in systemic sclerosis (scleroderma) which occurs prior to tissue fibrosis Flavahan et al., "Increased Alpha2-Adrenergic Constriction of Isolated Arterioles in Diffuse Scleroderma," *Arthritis and Rheumatism*, 43:1886–1890 (2000), which is herein incorporated by reference in its entirety).

In 95% of the patients with Raynaud's disease, the earliest manifestation of systemic sclerosis is a vasospastic response of the digital arteries to cold exposure. A blood vessel wall defect associated with Raynaud's disease was postulated by Lewis in 1929 (Lewis et al., "Experiments Relating to the Peripheral Mechanism Involved in Spasmodic Arrest of the Circulation in Fingers: A Variety of Raynaud's Disease," *Heart*, 15:7–101 (1929), which is herein incorporated by reference in its entirety). Thus, the $\alpha_{2c}$-ARs are not functionally responsive at 37° C., i.e. silent in normal regulation of the vascular function, but are activated by catecholamines at 28° C.

Stable cell lines expressing the human $\alpha_2$ adrenergic receptors described above as well as stable cell lines expressing the human $\alpha_1$ adrenergic receptors have been deposited with the American Type Culture Collection (ATCC), 12301 Parklawn Drive, Rockville, Md., 20852, U.S.A., under the provisions of the Budapest Treaty for the International Recognition of the Deposit of Microorganisms for the Purposes of Patent Procedure. The cell line expressing the human $\alpha_{2a}$ receptor is designated L-$\alpha_{2a}$ and was deposited on Nov. 6, 1992, under ATCC Accession Number CRL-11180. The cell line expressing the human $\alpha_{2b'}$ receptor is designated L-NGC-$\alpha_{2b}$ and was deposited on Oct. 25, 1989 under ATCC Accession Number CRL-10275. The cell line expressing the human $\alpha_{2c}$ receptor is designated L-$\alpha_{2c}$ and was deposited on Nov. 6, 1992, under ATCC Accession Number CRL-11181.

EXAMPLES

The Examples set forth below are for illustrative purposes only and are not intended to limit, in any way, the scope of the present invention.

Example 1

Synthesis of Yohimbine Dimers

The designed yohimbine dimers (3a–j) were prepared by coupling commercially available yohimbinic acid with aliphatic α,ω-diamines under standard peptide coupling condition as shown in the chemical reaction sequence below.

(The structures of bivalent yohimbines were confirmed by spectroscopic analysis (MS, IR. $^1$H NMR. $^{13}$C NMR) and elemental analysis. Due to the conformationally rigid nature of the yohimbine polycyclic ring system, (Morrison, G. A., *Fortscher. Chem. Organ. Naturstoffe*, 25:269 (1967), which is herein incorporated by reference in its entirety), the stereo centers that are susceptible to epimerization during the coupling reaction and the subsequent reaction work up are those at C16 and C17. However, the integrity of their stereochemistry was conserved as confirmed by decoupling NMR studies.

Example 2

Binding Selectivities for Yohimbine Dimers on Human $\alpha_{2a}$-versus $\alpha_{2b}$ Adrenergic Receptors The bivalent ligand approach has been successfully utilized in developing highly potent and selective ligands in a diverse set of receptor systems (Portoghese et al., "Stereostructure-activity Relationship of Opioid Agonist and Antagonist Bivalent Ligands: Evidence for Bridging Between Vicinal Opioid Receptors," *J. Med. Chem.*, 28:1140–1141 (1985); Erez et al., "Narcotic Antagonistic Potency of Bivalent Ligands Which Contain Beta-naltrexamine: Evidence for Bridging the Proximal Recognition Sites,"*J. Med. Chem.*, 25:847–849 (1982); Portoghese, "The Role of Concepts in Structure-activity Relationship Studies of Opioid Ligands," *J. Med. Chem.*, 35:1927–1937 (1992); Portoghese, "Bivalent Ligands and the Message-address Concept in the Design of Selective Opioid Receptor Antagonists," *TIPS* 10:230–235 (1989); Shimohigashi et al., "Dimeric Tetrapeptide Enkephalins Display Extraordinary Selectivity for the Delta Opiate Receptor," *Nature*, 297:333–335 (1982); LeBoulluec et al., "Bivalent Indoles Exhibiting Serotonergic Binding Affinity," *Bioorg. Med. Chem. Lett.*, 5:123–126 (1995); Cwirla et al., "Peptide Agonist of the Thrombopoietin Receptor as Potent as the Natural Cytokine," *Science*, 276:1696–1699 (1997), each of these references is hereby incorporated by reference in its entirety), such as the opioid and serotonergic receptors, two members of the seven transmembrane G protein-coupled receptor super-family, as well as the growth factor receptor system.

In these studies of the present invention, it was demonstrated that bivalent ligands exhibit a higher degree of potency and selectivity than their monovalent counterparts. This superior activity of bivalent ligands was shown to result from the bridging between either vicinal receptors or the pharmacophore binding site and another accessory site in the same receptor molecule (Portoghese et al., "Stereostructure-activity Relationship of Opioid Agonist and Antagonist Bivalent Ligands: Evidence for Bridging Between Vicinal Opioid Receptors," *J. Med. Chem.*, 28:1140–1141 (1985); Erez et al., "Narcotic Antagonistic Potency of Bivalent Ligands Which Contain Beta-naltrexamine: Evidence for Bridging the Proximal Recognition Sites," *J. Med. Chem.*, 25:847–849 (1982); Portoghese, "The Role of Concepts in Structure-activity Relationship Studies of Opioid Ligands," *J. Med. Chem.*, 35:1927–1937 (1992); Portoghese, "Bivalent Ligands and the Message-address Concept in the Design of Selective Opioid Receptor Antagonists," *TIPS*, 10:230–235 (1989); Shimohigashi et al., "Dimeric Tetrapeptide Enkephalins Display Extraordinary Selectivity for the Delta Opiate Receptor," *Nature*, 297:333–335 (1982), each of these references is hereby incorporated by reference in its entirety).

Evaluation of yohimbine dimers on human $\alpha_{2a}$-, $\alpha_{2b}$-, and $\alpha_{2c}$-AR expressed stably in Chinese hamster ovary (CHO) cells was conducted by displacement of radiolabeled rauwolsine using the various dimers. The binding affinities of yohimbine and these dimers are given in Table 1 below. [$^3$H]Rauwolscine was used as the radioligand in equilibrium competition binding experiments. Yohimbine was included as the monovalent compound against which bivalent yohimbines were compared.

TABLE 1

Binding affinities ($K_i$) of bivalent yohimbines on human
$\alpha_{2a}$ - and $\alpha_{2b}$ - AR expressed in CHO cells[a]

| Compound | N | Formula[b] | $K_i$ = SEM (nM)[c] $\alpha_{2a}$ - AR | $\alpha_{2b}$ - AR | $\alpha_{2a}/\alpha_{2b}$ Selectivity[d] |
|---|---|---|---|---|---|
| Yohimbine |   |   | 0.42 ± 0.04 | 2.01 ± 0.29 | 4.8 |
| 3a | 2 | $C_{42}H_{52}N_6O_4$-2HCl-2.5H$_2$O | 26.4 ± 7.3 | 1510 ± 262 | 57.2 |
| 3b | 3 | $C_{43}H_{54}N_6O_4$-2HCl-2H$_2$O | 52 ± 3.2 | 990 ± 85.2 | 19.0 |
| 3c | 4 | $C_{44}H_{56}N_6O_4$-2HCl-2H$_2$O | 15.3 ± 6.2 | 188.6 ± 38.1 | 12.3 |
| 3d | 5 | $C_{45}H_{58}N_6O_4$-2HCl-1.8H$_2$O | 1.73 ± 0.26 | 134.3 ± 38.1 | 77.6 |
| 3e | 6 | $C_{46}H_{60}N_6O_4$-2HCl-3H$_2$O | 1.35 ± 0.27 | 166.2 ± 56.7 | 123.1 |
| 3f | 7 | $C_{47}H_{62}N_6O_4$-2HCL-3H$_2$O | 0.87 ± 0.18 | 27.6 ± 4 | 31.7 |
| 3g | 8 | $C_{48}H_{64}N_6O_4$-2HCl-2.2H$_2$O | 0.76 ± 0.12 | 46 ± 7.6 | 60.5 |
| 3h | 9 | $C_{49}H_{66}N_6O_4$-2HCl-2.5H$_2$O | 1.25 ± 0.29 | 44.7 ± 1.9 | 35.8 |
| 3i | 10 | $C_{50}H_{68}N_6O_4$-2HCl-2.5H$_2$O | 0.39 ± 0.08 | 18.6 ± 1.6 | 47.7 |
| 3j | 12 | $C_{52}H_{72}N_6O_4$-2HCl-2.5H$_2$O | 1.18 ± 0.38 | 18.5 ± 0.57 | 15.7 |

[a]Data represent the mean ± SEM of four to nine experiments. [$^3$H]Rauwolscine (2.54 nM) was used as the radioligand in the equilibrium competition binding assays, and the nonspecific binding was measured in the presence of 10 μM of yohimbine.
[b]C, H, N analyses were within 0.4% of theory.
[c]$K_i$ (nM) was calculated according to the Cheng-Prusoff equation $K_i = IC_{50}/(1 - [L]/K_d)$ from determined $IC_{50}$ values. $K_d$ values for [$^3$H]rauwolscine at human $x_{2a}$- and $x_{2b}$-AR expressed in CHO cells were from Beeley et al., "Synthesis of a Selective Alpha-2A Advenoceptor Antagonist, BRL48962, and its Characterization at Cloned Human Alpha-adrenoceptors," Bioorg. Med. Chem., 3:1693–1698 (1995), which is herein incorporated by reference in its entirety.
$$\frac{K_i(x_{2a})}{K_i(x_{2b})}$$
[d]$\alpha_{2a}/\alpha_{2b}$ Selectivity = $K_1(\alpha_{2b})/K_1(\alpha 2a)$ Several features are evident from the data in Table 1.

Firstly, all of the yohimbine dimers displayed equal or lower affinity than the parent antagonist for the $\alpha_{2a}$ subtype; affinity for the $\alpha_{2b}$ adrenoceptor was reduced to a much greater extent. The lack of enhanced affinity of a dimer for either subtype may imply that the spacers of these bivalent ligands are not long enough to achieve the bridging of vicinal receptors. This consideration has been the basis for preparing further bivalent yohimbines of the present invention with longer spacers which are being evaluated at the $\alpha_2$-AR subtypes. This decision to prepare the dimers of the present invention with longer spacers was also facilitated by recent reports showing that receptor cluster formation was observed immunomicroscopically for the $\alpha_{2a}$-AR (Uhlen et al., *Pharmacol. Commun.*, 6, 155 (1995), which is herein incorporated by reference in its entirety) and that $\alpha_{2a}$- and $\alpha_{2c}$-AR can exist as dimers (Maggio et al., "Coexpression Studies with Mutant Muscarinic/Adrenergic Receptors Provide Evidence for Intermolecular "Cross-talk" Between G-Protein-linked Receptors," *Proc. Natl. Acad. Sci. USA*, 90:3103–3107 (1993); Maggio et al., "Functional Role of the Third Cytoplasmic Loop in Muscarinic Receptor Dimerization," *J. Biol. Chem.*, 271:31055–31060 (1996), each of these references is herein incorporated by reference in its entirety).

Secondly, lower binding affinities were observed for all bivalent yohimbines on the $\alpha_{2b}$ than the $\alpha_{2a}$ subtype. The highly divergent extracellular loops between the $\alpha_{2a}$ and $\alpha_{2b}$ subtype, in contrast to their highly homologous seven transmembrane regions, may have imparted the differential affinities of yohimbine dimers on the $\alpha_{2a}$ and $\alpha_{2b}$ subtypes (Harrison et al., "Molecular Characterization of Alpha1- and Alpha2-adrenoreceptors," *TIPS*, 12:62–67 (1991); Aantaa et al., "Molecular Pharmacology of Alpha2-adrenoreceptor Subtypes," *Ann. Med.*, 27:439–449 (1995), each of these references is hereby incorporated by reference in its entirety).

One prominent feature of this extracellular loop diversity between $\alpha_{2a}$- and $\alpha_{2b}$-AR is the differential distribution of acidic and basic amino acid residues in these loops. Basic residues are in a preponderance over acidic residues at $\alpha_{2b}$-AR, compared to their distributions at the $\alpha_{2a}$-AR. If it is assumed that the extracellular loop amino acid residues have the same $pK_a$ values when they are in the loop microenvironment and when they are free in the solution, the extracellular loops of the $\alpha_{2b}$-AR are more positively charged than the extracellular loops of the $\alpha_{2a}$-AR under our biological evaluation condition (pH=7.4).

Therefore, the binding of one protonated yohimbine moiety of the bivalent yohimbines at the receptor active site, which is within the seven transmembrane regions (Hieble et al., "Alpha- and Beta-adrenoreceptors: From the Gene to the Clinic," *J. Med. Chem.*, 38:3415–3444 (1995); Harrison et al., "Molecular Characterization of Alpha1- and Alpha2-adrenoreceptors," *TIPS*, 12:62–67 (1991), each of these references is hereby incorporated by reference in its entirety), will inevitably place the second protonated yohimbine moiety in an environment where strong electronic repulsion between the protonated yohimbine moiety and the highly positively charged extracellular loops of the $\alpha_{2b}$-AR is expected. This destabilizing electronic effect is expected to disturb the binding process of the yohimbine at the $\alpha_{2b}$-AR active site, thus, lower binding affinities were observed. However, on the $\alpha_{2a}$-AR, the weak electronic repulsion between the much less positively charged extracellular loops and the protonated yohimbine moiety is not expected to strongly disturb the binding of the yohimbine at the receptor active site. Furthermore, $\alpha_{2A(a)}$-AR from both native tissues and model cell lines are highly glycosylated at the extracellular N-terminal region (Wilson et al., "Monovalent Cation and Amiloride Analog Modulation of Adrenergic Ligand Binding to the Unglycosylated Alpha2B-adrenergic Receptor Subtype," *Mol. Pharmacol.*, 39:481–486 (1991); Guyer et al., "Cloning, Sequencing, and Expression of the Gene Encoding the Porcine Alpha2-adrenergic Receptor," *J. Biol. Chem.*, 265:17307–17317 (1990), each of these references is hereby incorporated by reference in its entirety), whereas $\alpha_{2B(b)}$-AR is not (Zeng et al., "Molecular Characterization of a Rat Alpha2B-adrenergic Receptor," *Proc. Natl. Acad. Sci. USA*, 87:3102–3106 (1990); Lanier et al., "Identification of Structurally Distinct Alpha2-adrenergic Receptors," *J. Biol. Chem.*, 263:14491–14496 (1988), each of these references is hereby incorporated by reference in its entirety). It is likely that the complex carbohydrate trees of the $\alpha_{2a}$ subtype shield the exposed charge, and thus further attenuate the electronic repulsion between extracellular loops and protonated yohimbine. A higher binding affinity was thus observed for a yohimbine dimer on the $\alpha_{2a}$ than on the $\alpha_{2b}$ subtype.

All yohimbine dimers identified above displayed binding selectivities for human $\alpha_{2a}$-versus $\alpha_{2b}$-ARs expressed in CHO cells, with peak selectivity occurring for 3e (n=6). Four of these dimeric compounds, i.e. 3d (n=5), 3e (n=6), 3g (n=8), 3i (n=10) represent the most potent and selective (48-fold to 123-fold) ligands identified so far for human $\alpha_{2a}$-versus $\alpha_{2b}$-ARs expressed in CHO cells.

Example 3

Binding Selectivities for Yohimbine Dimers on Human $\alpha_{2c}$-versus $\alpha_{2a}$- or $\alpha_{2b}$-Adrenergic Receptors By virtue of the results reported in Example 2 above, an examination of the selectivity of the yohimbine dimers on $\alpha_{2c}$-versus $\alpha_{2a}$ or $\alpha_{2b}$-ARs was conducted.

Evaluation of yohimbine dimers on human $\alpha_{2b}$- and $\alpha_{2c}$-AR expressed stably in Chinese hamster ovary (CHO) cells was conducted as described above. The results are present in Table 2 below.

TABLE 2

Binding affinities of yohimbine and its bivalent analogs on human $\alpha_{2a}$-, $\alpha_{2b}$- and $\alpha_{2c}$- adrenoceptors (AR) expressed in CHO cells

| | pK$_i$ Values | | |
|---|---|---|---|
| Compound | $\alpha_{2a}$-AR | $\alpha_{2b}$-AR | $\alpha_{2c}$-AR |
| Yohimbine | 8.52 ± 0.04 | 8.00 ± 0.10 | 9.17 ± 0.02[b] |
| n = 2 (3a) | 7.03 ± 0.12 | 5.50 ± 0.07 | 8.45 ± 0.12[b] |
| n = 3 (3b) | 6.74 ± 0.03 | 5.69 ± 0.04 | 8.24 ± 0.07[b] |
| n = 4 (3c) | 7.27 ± 0.15 | 6.40 ± 0.08 | 8.08 ± 0.17[b] |
| n = 5 (3d) | 8.21 ± 0.07 | 6.55 ± 0.10 | 7.97 ± 0.13[a] |
| n = 6 (3e) | 8.35 ± 0.10 | 6.54 ± 0.16 | 8.16 ± 0.04[a] |
| n = 7 (3f) | 8.51 ± 0.08 | 7.24 ± 0.07 | 8.47 ± 0.11[a] |
| n = 9 (3g) | 8.40 ± 0.12 | 7.03 ± 0.02 | 8.63 ± 0.10[a] |
| n = 18 (3k) | 7.34 ± 0.10 | 6.60 ± 0.04 | 8.43 ± 0.01[b] |
| n = 24 (3j) | 6.39 ± 0.10 | 5.41 ± 0.02 | 8.30 ± 0.10[b] | pK$_i$ Values are the negative log of the Ki value, determined using the Cheng and Prusoff equation: K$_i$ = [IC$_{50}$]/(1 + [RL]/K$_{RL}$). [$^3$H]Rauwolscine was the radioligand (RL) used. Values are expressed as the mean ± SEM of n = 4–6 experiments. Statistical analysis was carried out by one-way analysis of variance (ANOVA) followed by Tukey's test.
Key:
[a]Indicates that the pKi values for the analog on the $\alpha_{2a}$-AR subtype are significantly different from the pKi values for the analog on the $\alpha_{2b}$- AR subtype; and
[b]Indicates that the pKi values for the analog on the $\alpha_{2c}$-AR subtype are significantly different from the pKi values on the $\alpha_{2a}$- and $\alpha_{2b}$-AR subtypes.

Figure 1:
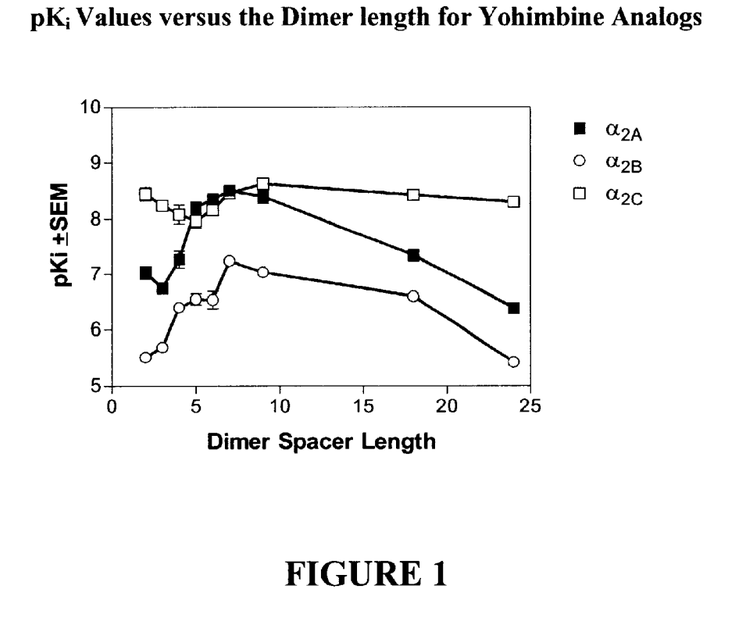
FIG. 1 shows a graph of P$_{ki}$ values versus dimer length for yohimbine analogs.

As can be seen in Table 2, all of the bivalent yobimbine analogs possess lower binding affinities on each of the three subtypes as compared to yohimbine. However in a closer evaluation, the dimeric analogs show much higher affinities for the $\alpha_{2a}$- and $\alpha_{2c}$-AR subtypes versus the $\alpha_{2b}$-AR at all linker lengths (from n=2 to n=24), and there were relatively small changes in the pKi values for these analogs on the $\alpha_{2c}$-AR subtype. If a comparision is made between the pKi values of the bivalent yohimbine analogs on the three $\alpha_2$-AR subtypes, there is a high degree of selectivity of yohimbine dimers for the $\alpha_{2c}$-AR subtype at spacers on n=2, 3, 4, 18 and 24 (see FIG. 1). In particular, it has been shown that the yohimbine dimer (n=24) binds with a potency for the $\alpha_{2c}$-AR which is 81- and 776-fold greater than its binding to the $\alpha_{2a}$- and $\alpha_{2b}$-ARs, respectively. It is particularly noteworthy that the addition of the methylene spacer linkages has produced analogs that are highly potent and selective $\alpha_{2c}$-AR ligands.

Taken collectively, these results indicate the following with regard to bivalent yohimbine compounds of the present invention: (1) All of the yohimbine dimers have higher affinities at the $\alpha_{2a}$- and $\alpha_{2c}$-AR as compared to the $\alpha_{2b}$-AR subtype; (2) Five of the dimeric compounds, i.e. n=2, n=3, n=4, n=18, and n=24, represent potent and selective ligands for the human $\alpha_{2c}$-AR subtype; (3) The findings provide support for demonstrating that the bivalent analog approach is useful for developing $\alpha_{2c}$-AR subtype selective ligands.

Example 4

Binding Selectivities for Yohimbine Dimers on Human $\alpha_{2c}$-versus $\alpha_1$-Adrenergic Receptors In addition, selected yohimbine dimers (n=3 and n=24) have been selected for further study of their potency profile of $\alpha_1$-AR subtype binding (see Table 3 below), and functional activities as antagonists of the human $\alpha_{2a}$- and $\alpha_{2c}$-AR.

TABLE 3

Binding affinities (pK$_i$ values) of yohimbine and its selective bivalent analogs (n = 3 and n = 24) on the human a $\alpha_1$- and $\alpha_{2c}$-AR subtypes expressed in HEK and CHO cells, respectively.

| Compound | $\alpha_{1a}$-AR | $\alpha_{1b}$-AR | $\alpha_{1d}$-AR | $\alpha_{2c}$ – AR |
|---|---|---|---|---|
| Yohimbine | 5.45 ± 0.05 | 5.52 ± 0.04 | 5.02 ± 0.01 | 9.17 ± 0.02 |
| n = 3 | 4.77 ± 0.05 | 5.24 ± 0.03 | 5.11 ± 0.05 | 8.24 ± 0.07 |
| n = 24 | 4.52 ± 0.01 | 4.91 ± 0.01 | 4.51 ± 0.08 | 8.30 ± 0.10 | pKi = -log Ki (Ki value was determined according to the Cheng-Prusoff equation) and the data are the mean ± SEM of n = 4–6. [$^3$H]Rauwolscine and [$^3$H]prazosin were used as the radioligands in the equilibrium competition radioligand binding assays for $\alpha_2$- and $\alpha_1$-ARs expressed in CHO and HEK cells; and nonspecific binding was measured in the presence of 10 μM of yohimbine and 10 μM phentolamine respectively.

In order to establish the $\alpha_2$ versus $\alpha_1$ AR subtype selectivity of the bivalent analogs, it was necessary to determine their binding affinities on the remaining $\alpha_1$-AR subtypes. The data given in Table 3 demonstrates that yohimbine and its two bivalent analogs bind with a much higher potency to the $\alpha_{2c}$-AR subtype as compared to the three $\alpha_1$-AR subtypes. The binding affinities of yohimbine, and the n=3 and n=24 dimers for the $\alpha_{2c}$-AR subtype were at least 4400-, 1000- and 2450-fold greater than those on the $\alpha_1$-AR subtypes, respectively. These findings confirm the binding selectivity of these ligands for the $\alpha_{2c}$-AR subtype.

Example 5

Activity of Yohimbine Dimer on Reversal of Medetomidine Mediated Inhibition of Forskolin-Induced cAMP Levels in CHO Cells Expressing $\alpha_2$-Adrenergic Receptor Subtypes In order to verify that the observed binding affinities of the yohimbine analogs correlate with the functional responses in the $\alpha_2$-AR subtypes, the antagonist effects of yohimbine and the two bivalent selective analogs (n=3 and n=24) have been examined for their reversal of medetomidine mediated inhibiton of forskolin-induced cAMP levels in $\alpha_{2a}$- and $\alpha_{2c}$-AR.

These experiments were conducted as follows: a fixed concentration of medetomidine (10 nM) was added to block the cAMP-induced increases by forskolin (5 $\mu$M). The concentration of medetomidine was chosen which produced at least a 50% inhibition of the forskolin alone response in the $\alpha_2$-AR subtypes expressing CHO cell lines. Controls of yohimbine, medetomidine and basal responses (solvent control) were included. The concentration-dependent effects of yohimbine and two bivalent analogs (n=3 and n=24) to antagonize the action of medetomidine are provided in Table 4 below. The changes in cAMP levels were assessed by luciferase activities using a 6 CRE-LUC reporter gene bioassay. Concentrations of yohimbine, bivalent analog (n=3 carbon linker) and bivalent analog (n=24 carbon linker) varying from 0.01 to 10 $\mu$M were used. The conditions of incubation were sequentially: the addition of yohimbine antagonist for 20 min; addition of medetomidine for 20 min; the addition of forskolin and incubation for 4 hours. The $EC_{50}$ values of the yohimbine analog for the reversal of medetomidine effect's were calculated using the GraphPad Prism program; and the data are expressed as the mean ±SEM of n=3–4 experiments. The data of $EC_{50}$ values for the yohimbine analogs are presented in Table 4 below.

TABLE 4

The blockade of medetomidine effects by yohimbine and dimeric analogs on human $\alpha_{2a}$- and $\alpha_{2c}$-ARs expressed in CHO cells.

| Compound | Effective Concentration-50 (nM ± SEM)[a] | | $\alpha_{2c}$-AR Selectivity Ratio[b] |
|---|---|---|---|
| | $\alpha_{2a}$-AR | $\alpha_{2c}$-AR | |
| Yohimbine | 32 ± 6.4 | 3.2 ± 2.6 | 10.0 |
| Yohimbine Dimer (n = 3) | 660 ± 210 | 15.8 ± 5.2 | 41.8 |
| Yohimbine Dimer (n = 24) | 3180 ± 470 | 110 ± 20 | 28.8 |

[a]Values were determined as the concentration of each yohimbine analog that reversed the effect of medetomidine to the maximum cAMP response of forskolin. [b]The $\alpha_{2c}$-AR selectivity ratio is expressed an the $EC_{50}$ value for the compound on the $\alpha_{2a}$-AR relative to the value on the $\alpha_{2c}$-AR subtype.

The results in Table 4 show that yohimbine and bivalent analogs (n=3 and n=24) were able to reverse the medetomidine effects on the $\alpha_{2c}$-AR at lower concentrations than those required for reversal on the $\alpha_{2a}$-AR. Yohimbine, and its bivalent analogs, n=3 and n=24 were 10-fold, 42-fold and 29-fold more potent at inhibiting the action of medetomidine on the $\alpha_{2c}$-AR versus the $\alpha_{2a}$-AR subtype, respectively. In addition, the data of these functional studies are in good agreement with the differences in binding affinities observed with these drugs on these two $\alpha_2$-AR subtypes.

In summary, these bivalent yohimbine dimers are highly potent, selective $\alpha_{2c}$-AR antagonists.

Example 6

Intravital Microscopy Studies on the Mouse Cremaster Muscle Using Yohimbine

Intravital microscopy is a powerful technique that permits the real-time study of microvasculature (MV) responses to drugs or changes in physiological conditions.

Male C57-BL mice age 7–8 weeks and weighing approximately 20 g were used for the study. Prior to surgery animals were anesthetized with an i.m. injection of 15 mL of Ketaset (87 mg ketamine/mL+13 mg xylazine/mL). Body temperature was maintained at ~37° C. by convective heating. The animal was supinated and a midline incision was made in the ventro-cervical region and the underlying tissues bisected laterally to expose the trachea. A tracheotomy was performed and the animal intubated directly with PE50 tubing to facilitate ventilation, and the wound closed. The left rear limb was incised to expose the femoral neurovascular bundle, and the femoral vein isolated and catheterized with PE10 tubing attached to a syringe of normal saline. Next, the animal was placed on a specially designed surgery board and the right testicle oriented over the glass translumination window and irrigation initiated warmed (~37° C.) physiological saline (4.3 mM $NaHCO_3$, 26.4 mM NaCl, 0.9 mM KCl, 0.4 mM $CaCl_2$, 0.2 mM $MgSO_4$) over the tissue. The scrotum was incised medically and the underlying fascia blunt dissected to expose the testicle. The apical portion of the cremaster muscle is pinned distally on the surgery board and the cremaster muscle incised along its long axis to expose the testicle. The testicle was then gently forced back into the inguinal canal, allowing the cremaster muscle to be pinned evenly around the translumination window.

All experiments were carried out using an industrial grade microscope (Nikon MM-11) with two light sources, bright field (Opti-Quip 75 W xenon) and fluorescent (Nikon 150 W mercury). The primary camera assembly consists of a chilled charged coupled device (CCD) and controller (Hamamastu C5985). The secondary camera assembly consists of a CCD camera (MTI CCD72) in conjunction with an intensifier (MTI GENIISYS). Experiments are viewed on a video monitor and recorded on digital tapes for off-line processing. The video images are analyzed off-line using the Meta-Morph software (Universal Imaging Co.) on a Dell Optiplex GX-1. Calibration of the software was done using a micrometer slide and measurements are defined in sm/pixel. An average of 5–7 measures per time point per vessel were made and, when possible, the time interval between measurements is 5 seconds or less for the first minute of the experiment.

The prepared animal was placed on the stage of the microscope on either the surgery board with the translumination window or on a stereotaxic frame. Exposed tissues were irrigated with warmed physiological saline. The tissues were allowed to equilibrate until normal blood flow was observed, during this time it is scanned at 10× for A1–A4 arterioles. The arterioles were tested for physiological tone by the administration of 0.1 mM adenosine. Vessels that did not demonstrate at least a 20% increase in diameter will not be considered for the experiment. After the arteriole returns to resting diameter (~10 min), yohimbine was administered systemically using the femoral vein. The blood pressure was monitored with a Kent Scientific XBP-1000 unit.

Figure 2:
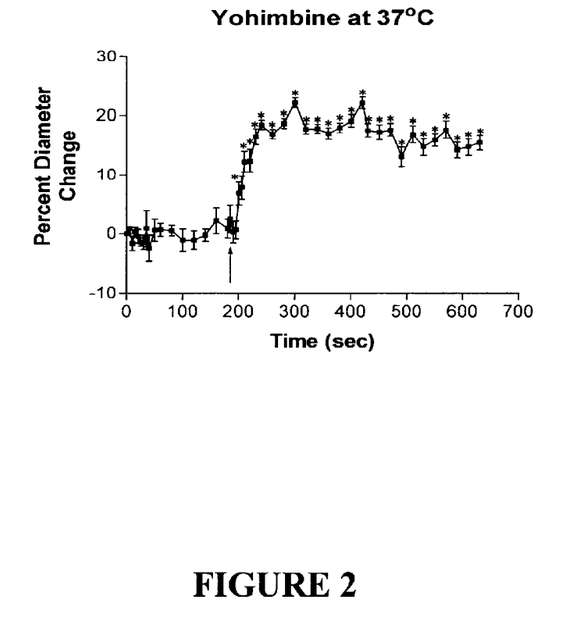
FIG. 2 shows a graph illustrating microvessel responses to vehicle and yohimbine administration. The first 180 sec represents the response to vehicle injection and the arrow indicates the time point associated with yohimbine injection. *=P<0.05, n=6.

Preliminary intravital studies at 37° C. on the cremaster muscle arterioles (A3–A4 resistance vessels) of male C57-BL mice have shown in detail the microvascular response to the treatment of animals with yohimbine. Administration of a vehicle solution did not affect the diameter of the observation vessel; however, subsequent treatment with yohimbine resulted in a 22.14±1.08 (n=6) percent increase in vessel diameter (FIG. 2). It is believed that the yohimbine dimers will similarly achieve this result.

The functional results observed are consistent with either the blockade of presynaptic or an interaction with post-synaptic $\alpha_2$-ARs. Therefore, preparations are being made to cool the tissue to 28° C. to evaluate if the resting diameter of the resistance vessels decreases, i.e., indicating the possible induction of $\alpha_{2c}$-ARs. It is believed the yohimbine dimers will antagonize the effects of temperature reduction.

DISCUSSION

Based upon molecular modeling studies, it is believed that several yohimbine dimers (n=18 or 24) have one pharmacophore binding at the regular binding site for yohimbine and the second pharmacophore binding to an adjacent site, possibly one of the extracelluar loops, on the same $\alpha_2$-AR. The selectivity may arise from the interaction of one of the pharmacophores with the regular binding site and the other pharmacophore binding with one of the extracellular loops within the same receptor rather than binding with two different receptors as originally believed in the art. Studies conducted with yohimbine compounds of the present invention examine the important make up of bivalent molecules to bind with one AR receptor (short linker), as observed with the yohimbine dimers of n=2, 3 and 4; and to two receptors by dimers with n=18 and 24 or greater (long linkers). Yohimbine dimer compounds of the present invention have been synthesized with longer linkers (wherein the integer n=20 and 36) and studied for interaction between AR receptors.

Based on molecular modeling docking studies of yohimbine, it is believed that there is an unexplored hydrophobic pocket in the receptor. At present it is unclear as to the exact mechanism underlying the selectivity; however, considering the similarity in the ligand binding domains and limited accessible space within the pocket, it is proposed that specific interactions with the extracellular loops plays a critical role in the selectivity. Interestingly, the chain length linking the yohimbine nucleus has only modest effects on $\alpha_{2c}$-AR selectivity; however, it appears to play a significant role in discriminating between on $\alpha_{2c}$-AR and the $\alpha_{2a}$- and $\alpha_{2b}$-AR subtypes. Based on these results, it is believed that extracellular loops to further enhance the receptor subtype selectivity by utilizing the extracellular loops as the address section on the novel dimer molecules.

Based on an amino acid alignment of the EL residues (Lomasney et al., "Molecular Biology of a-Adrenergic Receptors: Implications for Receptor Classification and for Structure-Function Relationships," *Biochim. Biophys. Acta.*, 1095:127–139 (1991); Dohlman et al., "A Family of Receptors Coupled to Guanine Nucleotide Regulatory Proteins," *Biochemistry*, 26:2657–2664 (1987), each of these references is hereby incorporated by reference in its entirety) and an analysis of the charged residues in these regions, it is believed that: (1) the chain lengths n=18 or greater atoms position the second yohimbine molecule into the ELs or into an adjacent receptor; (2) the extracellular domain of $\alpha_{2b}$-AR has a net positive charge (+8) distributed throughout the EL region and, therefore, the second yohimbine molecule (positively charged) is repulsed by the EL region to afford reduced binding affinity; and (3) the net negative charge of the $\alpha_{2c}$-AR (−2) combined with 10 hydrophobic residues (EL2 and 3) creates an ideal binding environment for the second yohimbine molecule. The profile for the $\alpha_{2c}$-AR and $\alpha_{2a}$-AR are less readily analyzed.

Interestingly, the chain length linking the yohimbine nucleus has only modest effects on $\alpha_{2c}$-AR binding affinity; the pK$_i$'s only varied between 7.97 to 8.63 (Table 2); however, it appears to play a significant role in discriminating between $\alpha_{2c}$-AR versus $\alpha_{2a}$- and $\alpha_{2b}$-AR subtypes. A qualitative analysis of the hydrophobic residues in EL2 (Gly[196]-Leu[204]) and EL3 (Ala[410]-Phe[418]) in the $\alpha_{2c}$-AR compared to those of the $\alpha_{2a}$- and $\alpha_{2b}$-AR (where EL2 and EL3 are interspersed with charged residues) indicates an important role in the binding of the yohimbine dimers to the $\alpha_{2c}$-AR (EL1 was excluded from the analysis based on the high sequence homology). Based on the EL analysis presented, a further enhancement of receptor subtype selectivity will be achieved by utilizing the charge negative, positive, or neutral message-addresses in such novel molecules of the present invention.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound according to formula (I)

(I)

wherein R is a linker molecule having a length of about 2.5 Å to about 45 Å.

2. The compound according to claim 1, wherein R has a length of about 2.5 Å to about 5 Å.

3. The compound according to claim 2, wherein R is a straight chain alkyl comprising 3 to 6 carbon atoms.

4. The compound according to claim 1, wherein R has a length of about 23 Å to about 29 Å.

5. The compound according to claim 4, wherein R is a straight chain alkyl comprising 12 to 24 carbon atoms.

6. The compound according to claim 1, wherein the compound exhibits selectivity in binding an $\alpha_{2a}$ adrenergic receptor over an $\alpha_{2b}$ adrenergic receptor.

7. The compound according to claim 1, wherein the compound exhibits selectivity in binding an $\alpha_{2c}$ adrenergic receptor over an a2b adrenergic receptor.

8. A compound according to formula (I)

(I)

wherein R is a straight or branched chain alkyl, alkenyl, alkynyl comprising at least 2 carbon atoms in a main chain thereof; or wherein R is a straight or branched chain alkyl, alkenyl, alkynyl comprising at least 2 carbon atoms in a main chain thereof and an X group within the main chain and/or a Y group as a substituent linked to a carbon atom in the main chain, with X being —O—, carbonyl, —NR$^1$— with R$^1$ being H or an alkyl, —C(O)NHR$^1$— with R$^1$ being an alkyl, —S—, sulfoxide, sulfonyl, or a cyclic or multicyclic ring with or without hetero atoms as ring members and including, optionally, one or more substitutions on the ring structure, and with Y being —OH, —NO$_2$, —CN, —C(O)H, —SH, a primary, secondary, or tertiary amine, a carboxylic acid, an ester, a keto group, —SO$_2$NH$_2$, or —SO$_2$NHR$^2$ with R$^2$ being an alkyl; or wherein R is a cyclic or multicyclic ring with or without hetero atoms as ring members and including, optionally, one or more substitutions on the ring structure(s).

9. The compound according to claim 8, wherein R is a straight chain alkyl.

10. The compound according to claim 9, wherein R is a straight chain C2 to C36 alkyl.

11. The compound according to claim 10, wherein R is a straight chain C3 to C24 alkyl.

12. The compound according to claim 8, wherein R is a straight chain alkyl comprising at least 4 carbon atoms and an X group within the straight chain, wherein X is a —O—.

13. The compound according to claim 12, wherein R is —(CH$_2$ CH$_2$—O—CH$_2$ CH$_2$)$_n$— wherein n is an integer from 1 to 6.

14. The compound according to claim 12, wherein R is —(CH$_2$ CH$_2$—O—CH$_2$—CH$_2$—O—CH$_2$ CH$_2$)$_n$— wherein n is an integer from 1 to 4.

15. The compound according to claim 8, wherein R is a straight chain alkyl comprising at least 5 carbon atoms and an X group within the straight chain, wherein X is —C(O)NHR$^1$— with R$^1$ being an alkyl.

16. The compound according to claim 15, wherein R is —(CH$_2$—NHC(O))$_n$—CH$_2$—CH$_2$—CH$_2$—CH$_2$ —(C(O)NH—CH$_2$)$_n$— wherein each n is independently an integer from 1 to 3.

17. The compound according to claim 8, wherein R is a straight chain alkenyl comprising at least 5 carbon atoms in a main chain thereof and an X group within the main chain, wherein X is —C(O)NHR$^1$— with R$^1$ being an alkyl.

18. The compound according to claim 17, wherein R is a cis isomer or a trans isomer of —(CH$_2$—NHC(O))$_n$— CH$_2$—CH=CH—CH$_2$—(C(O)NH—CH$_2$)$_n$— wherein each n is independently an integer from 1 to 3.

19. The compound according to claim 18, wherein R is a cis isomer.

20. The compound according to claim 18, wherein R is a trans isomer.

21. The compound according to claim 8, wherein the compound exhibits selectivity in binding an $\alpha_{2a}$ adrenergic receptor over an $\alpha_{2b}$ adrenergic receptor.

22. The compound according to claim 8, wherein the compound exhibits selectivity in binding an $\alpha_{2c}$ adrenergic receptor over an $\alpha_{2b}$ adrenergic receptor.

23. A pharmaceutical composition comprising:
   a compound according to claim 1 and
   a pharmaceutically acceptable carrier.

24. A pharmaceutical composition comprising:
   a compound according to claim 8 and
   a pharmaceutically acceptable carrier.

25. A method of making a yohimbine dimer comprising:
   reacting yohimbic acid with a di-amine according to the formula H$_2$N—R—NH$_2$ under conditions effective to yield a yohimbine dimer according to claim 1.

26. A method of making a yohimbine dimer comprising:
   reacting yohimbic acid with a di-amine according to the formula H$_2$N—R—NH$_2$ under conditions effective to yield a yohimbine dimer according to claim 8.

* * * * *